United States Patent [19]

Frost et al.

[11] Patent Number: 5,034,401
[45] Date of Patent: Jul. 23, 1991

[54] DERIVATIVES OF (1-HYDROXY-2-PIPERIDYLALKYL-INDOL-2-ONES, 2-QUINOLINONES, 2-BENZO(B)AZAPINONES, BENZIMIDAZOL-2-ONES, AND QUINAZOLIN-2-ONES, THEIR PREPARATION AND THEIR APPLICATION IN THERAPEUTICS

[75] Inventors: Jonathan Frost, Wissous; Patrick Lardenois, Bourg la Reine; Jean Bertin, Clamart; Alfred Saarmets, Sacy en Brie; Corinne Rousselle, Bourg Achard, all of France

[73] Assignee: Synthelabo, Paris, France

[21] Appl. No.: 378,094

[22] Filed: Jul. 11, 1989

[30] Foreign Application Priority Data

Jul. 12, 1988 [FR] France .................... 88 09449
Dec. 13, 1988 [FR] France .................... 88 16373

[51] Int. Cl.$^5$ .................... A61K 31/445; C07D 401/06
[52] U.S. Cl. .................... 514/323; 546/16; 546/18; 546/158; 546/193; 540/523; 544/230; 544/268; 514/278; 514/312; 514/213; 514/259
[58] Field of Search .................... 546/201, 200, 158, 16, 546/18, 193; 514/323, 278, 312, 213, 259; 540/523; 544/230, 268

[56] References Cited

U.S. PATENT DOCUMENTS

| | | | |
|---|---|---|---|
| 3,217,011 | 11/1965 | Zenitz .................... | 546/201 |
| 4,455,422 | 6/1984 | Banno et al. .................... | 546/157 |
| 4,460,593 | 7/1984 | Banno et al. .................... | 546/158 |
| 4,567,187 | 1/1986 | Banno et al. .................... | 546/158 |
| 4,619,932 | 10/1986 | Banno et al. .................... | 546/158 |
| 4,711,899 | 12/1987 | Gaudilliere et al. .................... | 514/330 |

FOREIGN PATENT DOCUMENTS

| | | | |
|---|---|---|---|
| 0099766 | 2/1984 | European Pat. Off. .................... | 546/201 |
| 0202164 | 11/1986 | European Pat. Off. .................... | 546/158 |
| 2071094 | 9/1981 | United Kingdom .................... | 546/158 |

OTHER PUBLICATIONS

*Chemical Abstracts* 87:53098r, K. Nakagawa et al., "Carbostyril Derivatives", p. 453 (1977).
*Chemical Abstracts* 86:189739n, H. Fukushima et al., "4-(3-Substituted Amino-2-Hydroxy)Propoxy 2-Alkyl...", p. 592 (1977).

*Primary Examiner*—Richard L. Raymond
*Assistant Examiner*—Mark W. Russell
*Attorney, Agent, or Firm*—Wegner, Cantor, Mueller & Player

[57] ABSTRACT

A compound, in the form of a pure optical isomer or a mixture thereof, of formula (I):

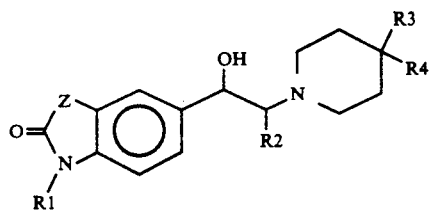

in which:
Z represents a group of formula —CH$_2$—, —C(CH$_3$)$_2$—, —CH=CH—, —(CH$_2$)$_2$—, —(CH$_2$)$_3$—, —NH— or —N(CH$_3$)CH$_2$—, in which the nitrogen is bonded to the carbonyl group;
R1 represents hydrogen or a C$_1$-C$_4$ alkyl group;
R2 represents hydrogen or a methyl group; and
R3 represents:
a phenoxy group which is unsubstituted or substituted by a halogen or a methyl group,
a naphthyloxy group,
a phenylmethyl group substituted by a halogen or a methyl group,
an unsubstituted phenylmethyl group when Z does not represent
a group of formula —CH=CH— or —(CH$_2$)$_2$—,
a bis (4-fluorophenyl)-methyl group,
a phenylmethoxy group which is unsubstituted or substituted by a halogen or a methyl group,
a (2-naphthyl)methoxy group,
a phenoxymethyl group which is unsubstituted or substituted by a halogen or a methyl group, or
a pyridinyloxy group, and
R4 represents hydrogen; or
R3 and R4 form, together and with the piperidine ring to which they are attached, a spiro (2,3-dihydrobenzofuran-2,4'-piperid-1-yl) group; or a pharmacologically acceptable acid addition salt thereof.

14 Claims, No Drawings

DERIVATIVES OF (1-HYDROXY-2-PIPERIDYLALKYL-INDOL-2-ONES, 2-QUINOLINONES, 2-BENZO(B)AZAPINONES, BENZIMIDAZOL-2-ONES, AND QUINAZOLIN-2-ONES, THEIR PREPARATION AND THEIR APPLICATION IN THERAPEUTICS

The present invention has as its subject derivatives of (1-hydroxy-2-piperidylalkyl)-indol-2-ones, 2-quinolinones, 2-benzo[b]azapinones, benzimidazol-2-ones and quinazolin-2-ones, their preparation and their application in therapeutics.

The present invention provides a compound in the form of a pure optical isomer or a mixture thereof, of formula (I):

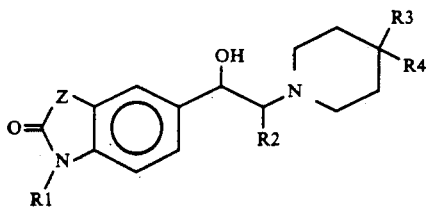

in which:
  Z represents a group of formula —CH$_2$—, —C(CH$_3$)$_2$—, —CH=CH—,—(CH$_2$)$_2$—, —(CH$_2$)$_3$—, —NH— or —N(CH$_3$)CH$_2$—, in which the nitrogen is bonded to the carbonyl group;
  R1 represents hydrogen or a C$_1$-C$_4$ alkyl group;
  R2 represents hydrogen or a methyl group; and
  R3 represents:
  a phenoxy group which is unsubstituted or substituted by a halogen or methyl group,
  a naphthyloxy group,
  a phenylmethyl group substituted by a halogen or a methyl group,
  an unsubstituted phenylmethyl group when Z does not represent a group of formula —CH=CH— or —(CH$_2$)$_2$—,
  a bis(4-fluorophenyl)-methyl group,
  a phenylmethoxy group which is unsubstituted or substituted by a halogen or a methyl group,
  a (2-naphthyl)methoxy group,
  a phenoxymethyl group which is unsubstituted or substituted by a halogen or a methyl group, or
  a pyridinyloxy group, and
  R4 represents hydrogen; or
  R3 and R4 form, together and with the piperidine ring to which they are attached, a spiro(2,3-dihydrobenzofuran2,4'-piperid-1-yl) group; or a pharmacologically acceptable acid addition salt thereof.

R1 is preferably hydrogen or an ethyl group.

R3 is preferably any one of the groups mentioned in the Table. The phenyl moieties are generally substituted in the 4-position, and the halogen substituents are generally fluorine, chlorine or bromine.

When the compound of formula (I) is in the form of a salt, it may, for example, be in the form of a fumarate salt.

Compounds analogous to those of present invention are described in C.A., 86, 189739n, C.A., 87, 53098r, in U.S. Pat. No. 4,455,422, U.S. Pat. No. 4,460,593, U.S. Pat. No. 4,567,187, U.S. Pat. No. 4,619,932 and U.S. Pat. No. 4,711,899, and in EP-A-0,099,766.

When R2 designates hydrogen, the compounds of formula (I) contain a single asymmetric carbon atom. They may therefore be in the form of pure enantiomers or of their mixtures.

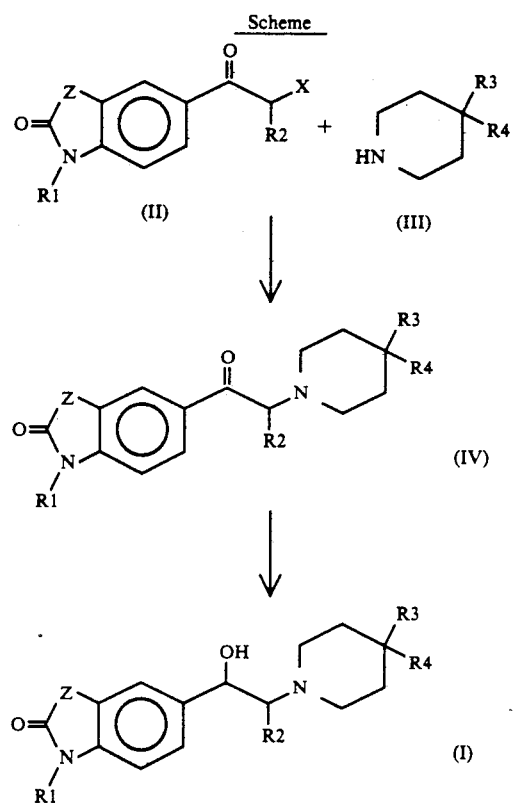

Scheme

When R2 designates a methyl group, the compounds of formula (I) contain two neighbouring asymmetric carbon atoms. There are therefore two diastereoisomeric forms, erythro and threo, each one of which comprises two enantiomers. The invention comprises each o f these pure forms, as well as their mixtures.

In accordance with the invention compounds of formula (I) may be prepared by a process illustrated by the preceding Scheme.

Thus the present invention provides a process for the preparation of a compound of formula (I) in which a ketone of formula (IV):

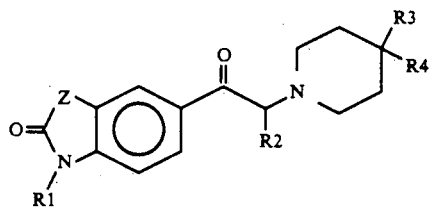

in which Z, R1, R2, R3 and R4 are as defined above, is reduced with sodium or potassium borohydride, and the compound of formula (I) thus obtained is, if desired, converted to a pharmacologically acceptable acid addition salt thereof. A halogenated ketone of formula (II), in which Z, R1 and R2 are as defined above and X represents a halogen atom such as chlorine or bromine, is reacted with a piperidine of formula (III), in which R3 and R4 are as defined above, and the ketone of general formula (IV) thus obtained is then reduced.

The two steps of the above process are reactions of types which are well known to those skilled in the art. The first step, a reaction between a halogenated derivative and a secondary amine, may take place, for example, in the presence of an inorganic base such as sodium carbonate or potassium carbonate, r,r in the presence of an excess of the piperidine of formula (III), in a solvent such as a $C_{1-6}$ or $C_{1-4}$ alcohol or acetoritrile, and if necessary in the presence of water. The second step, reduction of a ketone to an alcohol, may be carried out, for example, with sodium or potassium borohydride, in an alkaline or acid medium.

The optical isomers of a compound of formula (I) may be isolated from their mixtures according to any method.

The ketones of formula (II) in which Z represents —$CH_2$— and R1 represents H may be obtained from 3H-indol-2-one and chloroacetyl chloride or 2-chloropropanoyl chloride, in the presence of aluminium chloride, as described in EP-A- 0,168,003. The ketones of formula (II) in which Z represents —$C(CH_3)_2$— and R1 represents H may be obtained from 3,3-dimethyl-3H-indol-2-one, as described in J. Med. Chem., 29. 1832–1840 (1986) by reaction with chloroacetyl chloride or 2-chloropropanoyl chloride, in the presence of aluminium chloride.

The ketones of formula (II) in which Z represents —$(CH_2)_2$— or —CH=CH— and R1 and R2 each represent H are described in Chem. Pharm. Bull. 34(2), 682–693 (1986).

Those in which R2 represents $CH_3$ may be obtained, in a manner analogous to the known method, from 2(1H)-quinolinone and 2-chloropropanoyl chloride.

The ketones of formula (II) in which Z represents a group of formula —$(CH_2)_2$- may be obtained from 3,4-dihydro-2-(1H)-quinolinone and chloroacetyl chloride or 2chloride or 2-chloropropanoyl chloride, in the presence of aluminium chloride, as described in Japanese Patent Application 118172/1976.

The ketones of formula (II) in which R1 represents an alkyl and Z represents a group of formula —$C(CH_3)_2$—, —CH=CH— or —$(CH_2)_2$— may be obtained, for example, from 3,3-dimethyl-3H-indol-2-one, from 2(1H)-quinolinone or from 3,4-dihydro-2-(1H)-quinolinone (described in Zh. Org. Khim., 7(8), 1715–1721 (1971) and in Rev. Latinoam. Quim., 9(4), 190–192 (1978)) by a conventional alkylation, for example with sodium hydride and an alkyl bromide.

It is self evident, in addition, that a compound of formula (I) in which Z represents —$CH_2$—$CH_2$—may be prepared from the analogous compound, in which Z represents —CH=CH—, by catalytic hydrogenation.

The ketones of formula (II) in which Z represents a group of formula —$(CH_2)_3$— may be obtained in two steps, first of all from 3,4-dihydro-2H-naphthylen-1-one oxime, by a Beckman rearrangement, as described in J. Am. Chem. Soc., 74, 5153–5155 (1952), and then by the action of chloroacetyl chloride or 2-chloropropanoyl chloride, under the conditions indicated above.

The ketones of formula (II) in which Z represents a group of formula —NH— and R2 represents a hydrogen atom may be obtained from benzimidazol-2-one and chloroacetyl chloride, in the presence of aluminium chloride, as described in C.A., 101, 211043h; those in which R2 represents a methyl group may be obtained in an analogous manner, by using 2-chloropropanoyl chloride in the place of chloroacetyl chloride.

The ketones of formula (II) in which Z represents a group of formula —$N(CH_3)CH_2$— may be obtained from 3-methyl3,4-dihydro-1H-quinazolin-2-one, described in J. Het. Chem., 25, 789 (1988), and from chloroacetyl chloride or 2-chloropropanoyl chloride, in the presence of aluminium chloride, as described in Chem. Pharm. Bull., 36(6), 2253, (1988).

Most of the piperidines of formula (III) are described in the literature. Those in which R3 represents a phenoxy group and R4 represents a hydrogen atom are described in J. Med. Chem., 17(9), 1000 (1974); that in which R3 represents a naphthyloxy group and R4 represents a hydrogen atom is described in U.S. Pat. No. 4,443,462; those in which R3 represents a substituted phenylmethyl group and R4 represents a hydrogen atom are described in EP-A-0,106,317; those in which R3 represents a phenylmethoxy group and R4 represents a hydrogen atom are described in EP-A-0,077,427; that in which R3 represents a (2-naphthyl)methoxy group and R4 represents a hydrogen atom is described in U.S. Pat. No. 4,529,730; those in which R3 represents a bis(4-fluorophenyl)methyl group and R4 represents a hydrogen atom are described in BE-A-836,394; those in which R3 represents a pyridinyloxy group and R4 represents hydrogen atom may be obtained from 1-phenylmethyl-4-piperidinol, firstly by the action of 2-fluoropyridine in the presence of sodium hydride, then catalytic debenzylation of the intermediate 1-phenylmethyl-4-(2-pyridinyloxy) piperidine: those in which R3 represents a phenoxymethyl group and R4 represents a hydrogen atom are described in C.A., 87 84828h; and finally spiro(2,3-dihydrobenzofuran-2,4'-piperidine) is described in J. Het. Chem., 18(4), 811 (1981).

The following Examples illustrate in detail the preparation of some compounds according to the invention. Microanalyses and the IR and NMR spectra confirm the structures of the products obtained.

The numbers indicated in brackets in the titles of the Examples correspond to those in the table given further on.

EXAMPLE 1

(Compound No. 6)

($\pm$)5-{2-[4-[(4-Fluorophenyl)methyl]-1-piperidyl]-1-hydroxyethyl)-3H-indol-2 -one a) 5-Chloroacetyl-3H-indol-2-one.

A suspension of 40 g (300 mmoles) of aluminium chloride and 22.53 g, that is 15.9 ml (200 mmoles) of chloroacetyl chloride in 60 ml dichloromethane is stirred for 15 min at ambient temperature.

Then 13.32 g (100 mmoles) 3H-indol-2-one are added, in small portions, and the mixture is heated under reflux for 40 min. The mixtur.e is poured onto 800 ml ice, stirred for 30 min, and the solid is separated by filtration, washed with water, then with a little ether, and dried. 21.9 g of ochre crystals are obtained, which are used as such in the following stage.

b) ($\pm$)5-{2-[4-[(4-Fluorophenyl)methyl]-1-piperidyl]-1-hydroxyethyl}-3H-indol -2-one A mixture of 4.78 g (22.8 mmoles) 5-chloroacetyl-3H-indol-2-one, 6.3 g (45.6 mmoles) dry potassium carbonate, 7.19 g (22.8 mmoles) 4-(4-fluorophenylmethyl)-piperidine benzoate and 60 ml ethanol is heated under reflux for 2 h.

The mixture is left to cool, 10 ml water and then 5 g potassium borohydride are added, the mixture is stirred for 3 h 30 min at ambient temperature, 200 ml water are added and the mixture is left to stand for 36 h.

Ethyl acetate is added, the mixture is stirred, the organic phase is separated, the aqueous phase is extracted with ethyl acetate, the organic phases are pooled, washed with water, dried over sodium sulphate and evaporated. 7.56 g of a pink foam are obtained, which is purified by chromatography on a silica column, eluting with a 96/4 mixture of dichloromethane/methanol. 3.92 g of product are thus obtained, which are recrystallized from ethanol. 2.87 g of pink crystals are finally isolated.

Melting point: 167–168°C.

EXAMPLE 2

(Compound No. 1)

(±)5-[1-Hydroxy-2-(4-phenoxy-1-piperidyl)ethyl]-3H-indol-2-one.

A mixture of 4.19 g (20 mmoles) 5-chloroacetyl-3H-indol-2-one 4 g dry sodium carbonate, 4.27 g (20 mmoles) 4-phenoxypiperidine hydrochloride and 100 ml ethanol is heated under reflux fo 1 h 15 min under an argon atmosphere. The mixture is left to cool, 10 ml water, then 8 g potassium borohydride are added and stirring is continued for 2 h 30 min at ambient temperature. A further 200 ml water are added, the mixture is stirred for 30 min and filtered, and the solid is washed with water and dried. 4.67 g of oohre orystals are obtained, which are purified by chromatography on a silica column, eluting with a 95/5 mixture of dichloromethane/ methanol.

2.95 g of product are thus obtained, which are recrystallized from ethanol. 2 g crystals are finally isolated.

Melting point: 182–183° C.

EXAMPLE 3

(Compound No. 19)

(±)5-[1-Hydroxy-2-(-4-phenylmethyl-1-piperidyl)ethyl]-3,3-dimethyl-3H-indol-2-one a) 5-Chloroacetyl-3,3-dimethyl-2H-indol-2-one 10.8 g (66.4 mmoles) 3,3-dimethyl-3H-indol-2-one are slowly added (in 1 h) to a suspension of 26 7 g (200 mmoles) aluminium chloride and 15 g, that is 10.58 ml (133 mmoles) chloroacetyl chloride in 60 ml dichloromethane, then the mixture is heated under reflux for 1 h 30 min. The brown suspension obtained is slowly poured into 500 ml ice-water, the mixture is stirred for 30 min and then filtered and the solid is washed with a little ether and dried. 16.3 g of crystals are obtained, which are used as such in the following step.

b) (±)5-[1-Hydroxy-2-(-4-phenylmethyl-1-piperidyl)ethyl]- 3-dimethyl-3H-indol -2-one A mixture of 5.42 g (22.8 mmoles) 5-chloroacetyl3,3-dimethyl-3H-indol-2-one, 3.15 g (22.8 mmoles) dry potassium carbonate, 4 g, that is 4 ml (22.8 mmoles) 4-phenylmethylpiperidine and 50 ml ethanol is heated under reflux for 2 h in an argon atmosphere. The mixture is cooled in an ice bath, 5 ml water and 10 g potassium borohydride are added and stirring is continued overnight at ambient temperature. About 200 ml water are added and then 300 ml ethyl acetate, the organic phase is separated off, the aqueous phase is extracted with two times 200 ml ethyl acetate and the organic phases are pooled, washed with water, dried over sodium sulphate and evaporated. 8 g of brown crystals are obtained. After recrystallization from ethanol, washing in ethanol and drying, 3.57 g of white crystals are finally isolated.

Melting point. 178–79° C.

EXAMPLE 4

(Compound no. 23)

(±)1-Ethyl-5-{1-hydroxy-2-[4-[(4-methylphenol)methyl]-1-piperidyl]ethyl}-3,3dimethyl-3H-indol-2-one A mixture of 5.2 g (20 mmoles) 5-Chloroaoetyl-3,3-dimethyl-1-ethyl-3H-indol-2-one, 2.82 g (20.4 mmoles) dry potassium carbonate, 3.86 g (20.4 mmoles) 4-[(4methylphenyl)methyl]piperidine and 50 ml ethanol is heated under reflux for 1 h 30 min under an argon atmosphere.

The mixture is left to cool, 10 ml water, then 10.5 g potassium borohydride are added, the mixture is stirred for 4 h at ambient temperature and 150 ml water are added.

The precipitate obtained is filtered off and dried in the presence of phosphorus pentoxide, and 7.39 g of orange crystals are obtained which are purified by chromatography on a silica column, eluting with a 97/3 mixture of dichloromethane/methanol. 5.95 g of oil are obtained, which are taken up in 30 ml hot ethanol, the solution is filtered and the filtrate is left to cool. A precipitate forms which is separated off by filtration, washed with ethanol and dried at 80° C. under vacuum. 3.37 g of white crystals are finally isolated.

Melting Point: 131–132° C.

EXAMPLE 5

(Compound no. 31)

(±)6-{2-[4-[Bis(4-fluorophenyl)methyl]-1-piperidyl]-1-hydroxyethyl}-3,4-dihydro -2(1H)-quinolinone neutral fumarate.

A mixture of 1.72 g (7.72 mmoles) 6-chloroacetyl3,4-dihydro-2(1H)-quinolinone, 2.5 g (7.72 mmoles) 4-[bis(4-fluorophenyl)methyl]piperidine hydrochloride, 1.5 g sodium carbonate and 50 ml ethanol is heated under reflux for 1 h 30 min.

The mixture is cooled in an ice bath, 4 ml water and then 4.8 g potassium borohydride are added, the mixture is stirred at ambient temperature for 12 h, 100 ml water are added, the mixture is stirred for a further 10 min and the precipitate is separated off by filtration. The precipitate is washed with water and then with hexane, and dried in the presence of phosphorus pentoxide. 3.36 g of base are obtained, which are dissolved in 30 ml ethanol, a small amount of insoluble matter is separated off by filtration, and 0.8 g fumaric acid is added. The mixture is heated under reflux for 15 min, left to cool and placed in an ice bath. The crystals formed (1.3 g) are filtered off and recrystallized from 70 ml propanol, 1.08 g neutral fumarate are finally isolated.

Melting point: 161–163° C.

EXAMPLE 6

(Compound no. 33)

(±)Erythro -6{(1-hydroxy-2-[spiro(2,3-dihydrobenzofuran-2,4'-piperid-1-yl)]propyl}-3,4-dihydro-2(1H)-quinolinone A mixture of 4 g (17 mmoles) 6-(2-chloropropanoyl)-3,4-dihydro-2(1H)-quinolinone, 3.2 g (17 mmoles) spiro(2,3-dihydrobenzofuran-2,4'-piperidine, 50 ml ethanol and 2 g sodium carbonate is heated under reflux for 6 h. The mixture is left to cool, the inorganic precipitate is separated off by filtration, and washed with ethanol, 50 ml acetic acid is added &:o the filtrate, and then, little by little, 7 g potassium borohydride. The mixture is stirred for 12 h, 200 ml water and ice and 70 ml concentrated ammonia are added, and the mixture is extracted with ethyl acetate. The organic base is separated off, washed, dried and evaporated, and the gummy residue is taken up in 50 ml ethanol, the mixture is stirred for 1 h at ambient temperature, and the white precipitate (2.7 g) is filtered off and recrystallized from 75 ml ethanol. 1.9 g of the compound are finally isolated.

EXAMPLE 7

(Compound no. 28)

(±)6-{1-Hydroxy-2-[4-oxy(1-naphthyl)-1-piperidyl]ethyl}3, 4-dihydro-2(1H)-quinolinone A mixture of 3.35 g (15 mmoles) 6-chloroacetyl-2,3-dihydro-2(1H)-quinolinone, 4 g (15 mmoles) (1-naphthyl)-4-oxypiperidine, 80 ml ethanol and 3 g sodium carbonate is heated under reflux for 2 h.

The mixture is cooled, 10 ml water and 8 g potassium borohydride are added, the mixture is stirred for 12 h, 150 ml water is added and the mixture is stirred for 30 min; the precipitate is filtered off and dried in the presence of phosphorus pentoxide, and the 5.5 g of product thus obtained are purified by chromatography on a silica column, eluting with a 9/1 mixture of dichloromethane/methanol.

4 g of product is obtained, which are recrystallized from 100 ml ethanol. 3.68 g of compound are finally isolated.

Melting point: 158–159° C.

EXAMPLE 8

(Compound no. 18)

(±)5-{1-Hydroxy-2-[4-(2-pyridinyloxy)-1-piperidyl]ethyl}-3H-indol-2-one a) 5-Chloroacetyl-3H-indol-2-one A suspension of 40 g (300 mmoles) aluminium chloride and 22.53 g, that is 15.9 ml (200 mmoles) chloroacetyl chloride in 60 ml dichloromethane is stirred for 15 min at ambient temperature.

Then 13.32 g (100 mmoles) 3H-indol-2-one are added in small portions and the mixture is heated under reflux for 40 min. The mixture is poured into 800 ml ice and water and stirred for 30 min, and the solid is separated off by filtration, washed with water and then with a little ether, and dried. 21.9 g of ochre of crystals are obtained, which are used as such in the following step.

b) 4-(2-Pyridinyloxy)piperidine

A mixture of 60.65 H (318 mmoles) 1-phenylmethyl-4-piperidinol, 500 ml dimethylformamide, 46.25 g, that is 41 ml (475 mmoles) 2-fluoropyridine and 17 g 50% sodium hydride in mineral oil is heated at 100° C. for 1 h. The mixture is cooled in an ice bath, 20 ml water are added, the mixture is stirred for 30 min and concentrated to a residual volume of about 200 ml. 1 1 iced water is added, the mixture is stirred at 0° C. for 30 min, and the precipitate is filtered off, washed and dried. 90.71 g 1-phenylmethyl-4-(2-pyridinyloxy)piperidine are thus isolated. Melting point: 75° C.

45 g of this are taken and subjected to hydrogenation in a Parr flask, in 250 ml ethanol and 60 ml 1 N hydrochloric acid, in the presence of 2.5 g 10% palladiumoncharcoal, at 50° C. under a hydrogen pressure of about 0.35 Mpa, for 4 h. The catalyst is separated off by filtration, 60 ml 4N hydrochloric acid are added to the filtrate, the latter is evaporated and the residue taken up in ethanol and evaporated, 100 ml 2-propanol are added to the residue and, after stirring, the crystals are separated off by filtration, washed with 2-propanol and dried. 34.38 g of the dihydrochloride are obtained in the form of white crystals.

Melting point: 192–194° C.

c) (±)5-{1-Hydroxy-2-[4-(2-pyridinyloxy)-1-piperidyl]ethyl}-3H-indol-2-one

A mixture of 4.19 g (20 mmoles) 5-chloroacetyl-3H-indol-2-one, 150 ml ethanol, 6 g sodium carbonate and 5 g 4-(2-pyridinyloxy)piperidine dihydrochloride is heated under reflux for 2 h 30 min. The mixture is cooled in an ice bath, 10 ml water and then 8 g potassium borohydride are added and stirring is continued at ambient temperature of1 h. 300 ml water are added, the mixture is extracted with ethyl acetate and the extract is evaporated and purified by chromatography on a silica column, eluting with a 96/4 mixture of dichloromethane/ methanol. After recrystallization in 2-propanol 1.88 g of pure compound are isolated.

Melting point: 164–165° C.

EXAMPLE 9

(Compound no. 45)

(±)6-{2-[4-[(4-fluorohenyl)methoxy]-1-piperidyl]-1-hydroxyethyl}-3,4-dihydro -2(1H)-quinolinone A mixture of 4.47 g (20 mmoles) 6-chloroacetyl-3,4-dihydro-1H-quinolinone, 5.98 g (20 mmoles) 4-[(4-fluorophenyl)methoxy]piperidine oxalate, 8 g sodium carbonate, 180 ml ethanol and 20 ml water is heated under reflux for 3 h. The mixture is left to cool, 10 g potassium borohydride are added, the mixture is stirred for 4 h at ambient temperature, the solvent is evaporated to a residual volume of about 80 ml, 30 ml water are added, the mixture is stirred for 15 min and the precipitate is separated off by filtration, centrifuged, dried and recrystallized from 50 ethanol. 3.08 g of crystals are finally isolated.

Melting point: 158–159° C.

EXAMPLE 10

(Compound no. 60)

(±)Erythro -7-{2-[4-[(4-fluorophenyl)methyl]-1-piperidyl]-1-hydroxypropyl)-1,3,4,5tetrahydrobenzo[b]-2-a-zapinone a) 7-(2-Chloro-1-oxopropyl)-1,3,4,5-tetrahydrobenzo[b]-2azapinone., A mixture of 28 g (210 mmoles) aluminium chloride, 16.6 g, that is 13 ml (130 mmoles) 2-chloropropanoyl chloride and 20 ml dichloromethane is stirred for 30 min at ambient temperature.

Then 11.7 g (73 mmoles) 1,3,4,5-tetrahydrobenzo[b]-2-azapinone are added in small portions and the mixture is heated under reflux for 3 h. It is left to cool, poured into 60ml ice and water and stirred for 30 min, and the solid is separated off by filtration, washed with water and hexane and dried. 6.4 g of product are obtained, which is used as such in the following step. Melting point: 136° C.

b) (±)Erythro -7-{2-[4-[(4-fluorophenyl)methyl]-1-piperidyl]1-hydroxypropyl}-1,3,4,5-tetrahydrobenzo[b]-2-azapinone A mixture of 3.77 g (15 mmoles) 7-(2-chloro-1-oxopropyl)-1,3,4,5-tetrahydrobenzo[b]-2-azapinone, 4.7 g (15 mmoles) [4-(4-fluorophenyl)methyl]piperidine benzoate, 3 g sodium carbonate and 200 ml ethanol is heated under reflux for 8 h. The mixture is left to cool, 50 ml acetic acid and 1ml water are added, and then, little by little, 10 g potassium borohydride. The mixture is stirred overnight at ambient &temperature, 250 ml ice-water is added and then, still cooling, 70 ml concentrated ammonia. The mixture is stirred for 15 min, the solid is filtered off and taken up in dichloromethane and water, the organic phase is separated off, dried over sodium sulphate and evaporated and the residue is recrystallized from propanol. 0.95 g of crystallized product are finally isolated.

Melting point: 195–196° C.

EXAMPLE 11

(Compound no. 76)

(±)Erythro -5-{1-hydroxy-2-[4-(phenylmethyl)-1-piperidyl]propyl}-1H-benzimidazol-2-one a) 5-(2-Chloro-1-oxopropyl)-1H-benzimidazol-2-one A suspension of 80 g (600 mmoles) aluminium chloride and 50.79 g, that is 39.83 ml (400 mmoles) 2-chloropropanoyl chloride in 120 ml dichloromethane is stirred for 15 min at ambient temperature.

Then 26.82 g (200 mmoles) 1H-benzimidazol-2-one are added in small portions, and when addition is complete, the mixture is heated under reflux for 1 h.

After cooling the mixture is poured into 1.5 l ice and water and stirred for 30 min, and the solid is separated off by filtration, washed with water and dried. 47.2 g grey crystals are obtained, which are used as such in the following step.

b) (±)Erythro -5-{1-hydroxy-2-[4-(phenylmethyl)-1-piperidyl]propyl}-1H-benzimidazol-2-one A mixture of 4.49 g (20 mmoles) 5-(2-chloro-1-oxopropyl)-1H-benzimidazol-2-one, 100 ml ethanol, 2 g sodium carbonate and 3.5 g, that is 3.52 ml (20 mmoles) 4-phenylmethylpiperidine is heated under reflux for 5 h. After cooling 50 ml acetic acid are added to the mixture, then 11 g potassium borohydride in small portions. Stirring is continued overnight 200 ml water are added, then concentrated ammonia &:o a basic pH, the mixture is extracted twice with ethyl acetate, the organic phase is washed with water and dried over magnesium sulphate, and the solvent is evaporated. 6.43 g of residue are obtained, which are purified by chromatography on a silica column, eluting with a 98/2 mixture of dichloromethane/ methanol. After recrystallization from ethanol 1.39 g of white crystals are finally obtained.

Melting point: 221–222° C.

EXAMPLE 12

(Compound no. 83)

(±)6-(1-Hydroxy-2-[4-(phenoxymethyl)-1-piperidyl]ethyl}-3-methyl-3,4-dihydro-1H-quinazolin-2-one A mixture of 3 g (12.6 mmoles) 6-chloroacetyl-3methyl-3,4-dihydro-1H-quinazolin-2-one, 2.4 g 4-(phenoxymethyl)piperidine, 1.7 g sodium carbonate, 70 ml ethanol and 15 ml water is heated under reflux for 2 h. The mixture is cooled, 6 g potassium borohydride are added slowly, and the mixture is allowed to return to ambient temperature while stirring. 125 ml water are added, the mixture is stirred for 1 h, then the solid is filtered off, washed with water, and recrystallized from ethanol. 5.1 g of compound are finally isolated.

Melting point: 205° C.

The following table illustrates the chemical structures and the physical properties of some compounds according to the invention.

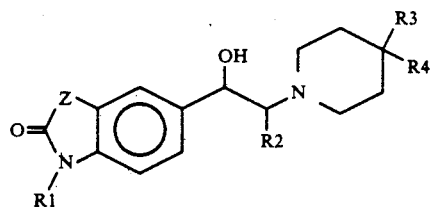

(±) if R2 = H
(±) erythro if R2 = CH3

| No | Z | R1 | R2 | R3 | R4 | Salt/base | m.p. (°C.) |
|---|---|---|---|---|---|---|---|
| 1 | —CH2— | H | H | —O—⌬ | H | base | 182–183 |
| 2 | —CH2— | H | H | —O—⌬—F | H | base | 165–167 |

-continued
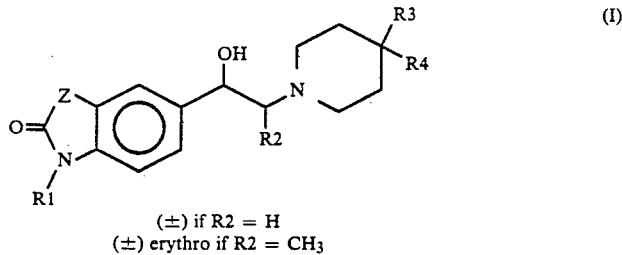
(±) if R2 = H
(±) erythro if R2 = CH₃
| No | Z | R1 | R2 | R3 | R4 | Salt/base | m.p. (°C.) |
|---|---|---|---|---|---|---|---|
| 3 | —CH₂— | H | H | —O-naphthyl | H | base | 200–201 |
| 4 | —CH₂— | H | CH₃ | —O-naphthyl | H | base | 157–158 |
| 5 | —CH₂— | H | H | —CH₂-phenyl | H | base | 178–179 |
| 6 | —CH₂— | H | H | —CH₂-C₆H₄-F | H | base | 167–168 |
| 7 | —CH₂— | H | H | —CH₂-C₆H₄-CH₃ | H | base | 205–206 |
| 8 | —CH₂— | H | CH₃ | —CH₂-phenyl | H | base | 195–197 |
| 9 | —CH₂— | H | CH₃ | —CH₂-C₆H₄-F | H | base | 183–184 |
| 10 | —CH₂— | H | CH₃ | —CH₂-C₆H₄-CH₃ | H | base | 187–189 |
| 11 | —CH₂— | H | CH₃ | —O-phenyl | H | base | 150–151 |
| 12 | —CH₂— | H | CH₃ | —O-C₆H₄-F | H | base | 154–155 |

-continued $$\text{(I)}$$

(±) if R2 = H
(±) erythro if R2 = CH₃

| No | Z | R1 | R2 | R3 | R4 | Salt/base | m.p. (°C.) |
|----|---|----|----|----|----|-----------|------------|
| 13 | —CH₂— | H | H | —OCH₂-(2-naphthyl) | H | base | 194–195 |
| 14 | —CH₂— | H | H | —OCH₂-phenyl | H | base | 202–203 |
| 15 | —CH₂— | H | H | —OCH₂-(4-F-phenyl) | H | base | 183–184 |
| 16 | —CH₂— | H | H | —OCH₂-(4-Cl-phenyl) | H | base | 184–185 |
| 17 | —CH₂— | H | H | —OCH₂-(4-CH₃-phenyl) | H | base | 162–163 |
| 18 | —CH₂— | H | H | —O-(2-pyridyl) | H | base | 164–165 |
| 19 | —C(CH₃)₂— | H | H | —CH₂-phenyl | H | base | 178–179 |
| 20 | —C(CH₃)₂— | H | H | —CH₂-(4-F-phenyl) | H | base | 190–191 |
| 21 | —C(CH₃)₂— | H | H | —CH₂-(4-CH₃-phenyl) | H | base | 178–180 |
| 22 | —C(CH₃)₂— | C₂H₅ | H | —CH₂-phenyl | H | base | 109–110 |

-continued
(I)
(±) if R2 = H
(±) erythro if R2 = CH3
| No | Z | R1 | R2 | R3 | R4 | Salt/base | m.p. (°C.) |
|----|---|----|----|----|----|-----------|------------|
| 23 | —C(CH₃)₂— | C₂H₅ | H | —CH₂—C₆H₄—CH₃ | H | base | 131–132 |
| 24 | —CH=CH— | H | H | —CH₂—C₆H₄—F | H | base | 234–235 |
| 25 | —(CH₂)₂— | H | H | —O—C₆H₅ | H | base | 191–192 |
| 26 | —(CH₂)₂— | H | CH₃ | —O—C₆H₅ | H | base | 210–211 |
| 27 | —(CH₂)₂— | H | CH₃ | —O—C₆H₄—F | H | base | 186–187 |
| 28 | —(CH₂)₂— | H | H | —O—naphthyl | H | base | 158–159 |
| 29 | —(CH₂)₂— | H | H | —CH₂—C₆H₄—F | H | base | 173–174 |
| 30 | —(CH₂)₂— | H | H | —CH₂—C₆H₄—CH₃ | H | base | 205–206 |
| 31 | —(CH₂)₂— | H | H | —CH(—C₆H₄—F)₂ | H | fum. | 161–163 |
| 32 | —(CH₂)₂— | H | H | 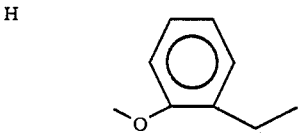 | | base | 211–212 |

-continued
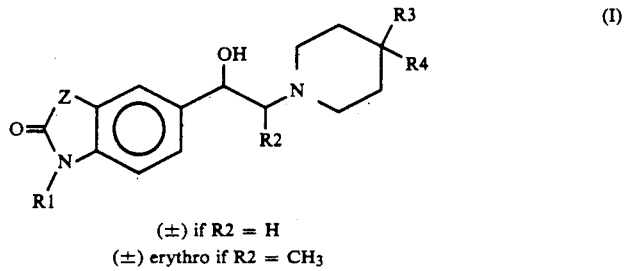
(±) if R2 = H
(±) erythro if R2 = CH3
| No | Z | R1 | R2 | R3 | R4 | Salt/base | m.p. (°C.) |
|---|---|---|---|---|---|---|---|
| 33 | —(CH2)2— | H | CH3 | 2-methoxy-6-ethylphenyl | | base | 195–196 |
| 34 | —(CH2)2— | C2H5 | H | —O-phenyl | H | base | 91–93 |
| 35 | —(CH2)2— | C2H5 | H | —CH2-(4-F-phenyl) | H | base | 100–103 |
| 36 | —(CH2)2— | C2H5 | H | —CH2-(4-CH3-phenyl) | H | base | 104–105 |
| 37 | —(CH2)2— | H | H | —O-(2-CH3-phenyl) | H | base | 158–159 |
| 38 | —(CH2)2— | H | H | —O-(1-naphthyl) | H | base | 158–159 |
| 39 | —(CH2)2— | H | CH3 | —O-(1-naphthyl) | H | base | 169–170 |
| 40 | —(CH2)2— | H | H | —OCH2-(2-naphthyl) | H | base | 204–205 |

-continued

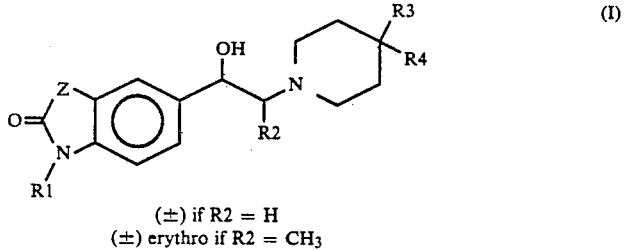

(±) if R2 = H
(±) erythro if R2 = CH3

| No | Z | R1 | R2 | R3 | R4 | Salt/base | m.p. (°C.) |
|----|---|----|----|----|----|-----------|------------|
| 41 | —(CH$_2$)$_2$— | H | CH$_3$ | —OCH$_2$-naphthyl | H | base | 175–176 |
| 42 | —(CH$_2$)$_2$— | H | H | —O-C$_6$H$_4$-F | H | base | 176–177 |
| 43 | —(CH$_2$)$_2$— | H | H | —O-C$_6$H$_4$-CH$_3$ | H | base | 190–191 |
| 44 | —(CH$_2$)$_2$— | H | H | —OCH$_2$-C$_6$H$_5$ | H | base | 171–172 |
| 45 | —(CH$_2$)$_2$— | H | H | —OCH$_2$-C$_6$H$_4$-F | H | base | 158–159 |
| 46 | —(CH$_2$)$_2$— | H | H | —OCH$_2$-C$_6$H$_4$-Cl | H | base | 187–188 |
| 47 | —(CH$_2$)$_2$— | H | CH$_3$ | —OCH$_2$-C$_6$H$_4$-F | H | base | 164–166 |
| 48 | —(CH$_2$)$_2$— | H | H | —OCH$_2$-C$_6$H$_4$-Br | H | base | 187–188 |
| 49 | —(CH$_2$)$_2$— | H | H | —OCH$_2$-C$_6$H$_4$-CH$_3$ | H | base | 158–160 |
| 50 | —(CH$_2$)$_2$— | H | H | —CH$_2$O-C$_6$H$_4$-F | H | base | 167–168 |
| 51 | —(CH$_2$)$_2$— | H | H | —CH$_2$O-C$_6$H$_4$-CH$_3$ | H | base | 199–200 |

-continued
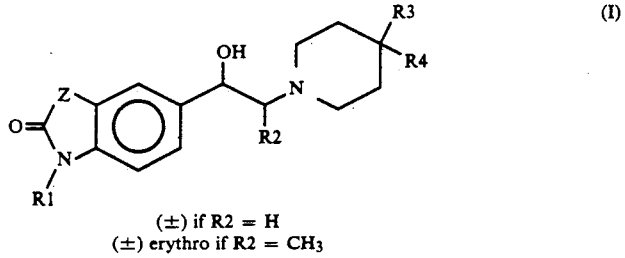
(±) if R2 = H
(±) erythro if R2 = CH3
| No | Z | R1 | R2 | R3 | R4 | Salt/base | m.p. (°C.) |
|---|---|---|---|---|---|---|---|
| 52 | —(CH2)2— | H | H | -O-pyridyl (N at 2-position) | H | base | 202–203 |
| 53 | —(CH2)3— | H | H | —CH2-C6H4-F | H | base | 186–188 |
| 54 | —(CH2)3— | H | H | —O-C6H5 | H | base | 192–193 |
| 55 | —(CH2)3— | H | H | —CH2-C6H5 | H | base | 173–174 |
| 56 | —(CH2)3— | H | H | —O-C6H4-F | H | base | 142–143 |
| 57 | —(CH2)3— | H | H | —O-C6H4-CH3 | H | base | 188–189 |
| 58 | —(CH2)3— | H | CH3 | —CH2-C6H5 | H | base | 197–198 |
| 59 | —(CH2)3— | H | CH3 | —O-C6H4-F | H | base | 194–195 |
| 60 | —(CH2)3— | H | CH3 | —CH2-C6H4-F | H | base | 195–196 |
| 61 | —(CH2)3— | H | CH3 | —O-C6H5 | H | base | 201–202 |
| 62 | —(CH2)3— | H | H | —OCH2-C6H5 | H | base | 163–164 |

-continued $$\text{(I)}$$

Structure: Bicyclic system with Z linking to a benzene ring fused to a 5-membered ring containing N-R1 and C=O; benzene bears a -CH(OH)-CH(R2)-N< group where N is part of a piperidine ring substituted at the 4-position with R3 and R4.

(±) if R2 = H
(±) erythro if R2 = CH3

| No | Z | R1 | R2 | R3 | R4 | Salt/base | m.p. (°C.) |
|----|---|----|----|----|----|-----------|------------|
| 63 | —(CH₂)₃— | H | H | —OCH₂—C₆H₄—F (4-F) | H | base | 156–157 |
| 64 | —(CH₂)₃— | H | H | —OCH₂—C₆H₄—Cl (4-Cl) | H | base | 162–163 |
| 65 | —(CH₂)₃— | H | H | —OCH₂—C₆H₄—Br (4-Br) | H | base | 173–174 |
| 66 | —(CH₂)₃— | H | H | —OCH₂—C₆H₄—CH₃ (4-CH₃) | H | base | 175–176 |
| 67 | —(CH₂)₃— | H | H | —CH₂O—C₆H₄—F (4-F) | H | base | 154–155 |
| 68 | —(CH₂)₃— | H | H | —CH₂O—C₆H₄—CH₃ (4-CH₃) | H | base | 189–190 |
| 69 | —NH— | H | H | —CH₂—C₆H₅ | H | base | 224–226 |
| 70 | —NH— | H | H | —CH₂—C₆H₄—F (4-F) | H | base | 231–232 |
| 71 | —NH— | H | H | —OCH₂—C₆H₅ | H | base | 238–239 |
| 72 | —NH— | H | H | —OCH₂—C₆H₄—F (4-F) | H | base | 237–238 |
| 73 | —NH— | H | H | —OCH₂—C₆H₄—Cl (4-Cl) | H | base | 248–250 |

-continued $$(I)$$

(±) if R2 = H
(±) erythro if R2 = CH₃

| No | Z | R1 | R2 | R3 | R4 | Salt/base | m.p. (°C.) |
|---|---|---|---|---|---|---|---|
| 74 | —NH— | H | H | —OCH₂—C₆H₄—Br | H | base | 253–254 |
| 75 | —NH— | H | H | —OCH₂—C₆H₄—CH₃ | H | base | 247–248 |
| 76 | —NH— | H | CH₃ | —CH₂—C₆H₅ | H | base | 221–222 |
| 77 | —NH— | H | H | —O—C₆H₅ | H | base | 252–254 |
| 78 | —NH— | H | H | —O—C₆H₄—F | H | base | 240–241 |
| 79 | —NH— | H | H | —O—C₆H₄—CH₃ | H | base | 237–238 |
| 80 | —NH— | H | H | —CH₂O—C₆H₄—CH₃ | H | base | 273–275 |
| 81 | —NH— | H | H | —O—(2-pyridyl) | H | base | 235–236 |
| 82 | —N(CH₃)—CH₂— | H | H | —OCH₂—C₆H₅ | H | base | 174 |
| 83 | —N(CH₃)—CH₂— | H | H | —CH₂O—C₆H₅ | H | base | 205 |

-continued

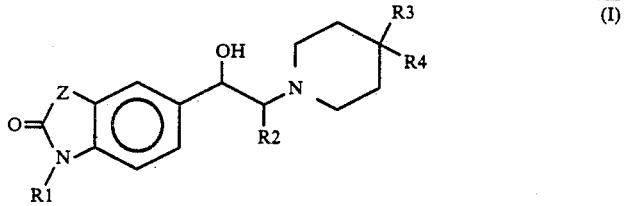

(±) if R2 = H
(±) erythro if R2 = CH3

| No | Z | R1 | R2 | R3 | R4 | Salt/base | m.p. (°C.) |
|---|---|---|---|---|---|---|---|
| 84 | —(CH2)3— | H | H | 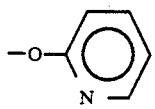 | H | base | 200 |

Note
In the "Salt/base" column, fum. indicates neutral fumarate.

The compounds of the invention have been the subject of various pharmacological studies which have shown their value as substances with therapeutic activity.

Thus, for example, they have been subjected to the global cerebral ischaemia test in the mouse. The ischaemia is due to a cardiac arrest induced by a rapid intravenous injection of magnesium' chloride. In this test the "survival time" is measured, that is to say the interval between the time of injection of magnesium chloride and the last observable respirator movement of each mouse. This last movement is considered as the final sign of any function of the central nervous system.

Respiratory arrest appears approximately 19 seconds after injection of magnesium chloride.

Male mice (Charles River CD1) are studied in groups of 10. They are fed and watered ad libitum before the experiments. The survival time is measured 10 minutes after intraperitoneal administration of the compounds of the invention. The results are given in the form of the difference between the survival time measured in a group of 10 mice which have received the compound and the survival time measured in a group of 10 mice which have received the liquid vehicle. The relationships between the modifications of the survival time and the dose of the compound are recorded graphically using a semilogarithmic curve.

This curve allows calculation of the "3 second effective dose" ($ED_3'$), that is to say the dose (in mg/kg) which produces a 3 second increase in the survival time with respect to a control group of 10 untreated mice.

An increase of 3 seconds in the survival time is both statistically significant and reproducible.

The $ED_3''$ of the compounds of the invention are of the order of 2 to 50 mg/kg by the intraperitoneal route.

In addition the applicant has found that they inhibit the stimulating effects of N-methyl-D-aspartate ("NMDA") on the level of cyclic guanosine 3',5'-monophosphate ("cGMP") in the cerebellum of the immature rat, following an experiment such as that described in J. Neurochem, (1987), 49. No. 1, 195-200.

The $IC_50$ concentrations, which inhibit 50% of the effects of NMDA, are cf the order of 0.3 µM for the compounds of the invention which are most active in this test.

The experiments carried out show that the compounds of the present invention are useful for the treatment and prevention of cerebral disorders such as those following, for example an ischeamic attack, a cardiac or respiratory arrest, a cerebral thrombosis or embolism or a cerebral trauma, for the treatment of cerebral senility, dementia following multiple infarcts, senile dementia, for example Alzheimer's disease or Pick's disease, and for the treatment of olivopontocerebellar and other neurodegenerative ailments such as Huntington's chorea, for the treatment of tinnitus, and for the treatment of certain cancers. The compounds of the present invention also have an antipsychotic activity, which makes them suitable, for example, for the treatment of schizophrenia.

Thus the present invention provides a compound of formula (I) or a pharmacologically acceptable acid addition salt thereof, or a composition as defined below, for use in a method of treatment of the human or animal body by therapy, in particular. for use in a method of treatment of a cerebral disorder, ischaemic attack, cardiac or respiratory arrest, cerebral thrombosis or embolism, cerebral trauma, ceretral senility, dementia following multiple infarcts, serile dementia, Alzheimer's disease, Pick's disease, tinnitus, cancer, sohizophrenia or an olivopontocerebellar or other neurodegenerative ailment.

The present invention also provides the use of a compound of formula (I) or a pharmacologically acceptable acid addition salt thereof in the manufacture of a medicament for the treatment of a cerebral disorder, ischaemic attack, cardiac or respiratory arrest, cerebral thrombosis or embolisx, cerebral trauma, cerebral senility, dementia following multiple infarcts, senile dementia, Alzheimer's disease, Pick's disease, tinnitus, cancer, schizophrenia or an olivopontocerebellar or other neurodegenerative ailment.

For this purpose the compounds of the present invention can be presented in all forms which are appropriate to their administration by the oral or parenteral route, in combination with all convenient excipients, and doses calculated to permit a daily posology of 1 to 1,000 mg.

The present invention therefore additionally provides a pharmaceutical composition which comprises a compound of formula (I) or a pharmacologically acceptable acid addition salt thereof and a pharmaceutically acceptable excipient.

We claim:

1. A compound, in the form of a pure optical isomer or a mixture thereof, of formula (I):

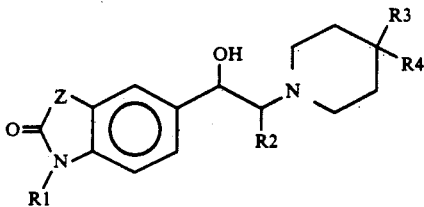

in which:
Z represents a group of formula —CH$_2$—, —C(CH$_3$)$_2$—, —CH=CH—, —(CH$_2$)$_2$—, —(CH$_2$)$_3$—, —NH— or —N(CH$_3$)CH$_2$—, in which the nitrogen is bonded to the carbonyl group;
R1 represents hydrogen or a C$_{1-4}$ alkyl group;
R2 represents hydrogen or a methyl group; and
R3 represents:
a phenoxy group which is unsubstituted or substituted by a halogen or a methyl group,
a naphthyloxy group,
a phenylmethoxy group which is unsubstituted or substituted by a halogen or a methyl group,
a (2-naphthyl)methoxy group,
a phenoxymethyl group which is unsubstituted or substituted by a halogen or a methyl group, or
a pyridinyloxy group, and
R4 represents hydrogen; or
R3 and R4 form, together and with the piperidine ring to which they are attached, a spiro(2,3-dihydrobenzofuran-2,4'-piperid-2-yl) group; or a pharmacologically acceptable acid addition salt thereof.

2. A compound according to claim 1 in which Z is —CH$_2$—.

3. A compound according to claim 1 in which Z is —C(CH$_3$)$_2$—.

4. A compound according to claim 1 in which Z is —(CH=CH—.

5. A compound according to claim 1 in which Z is —(CH$_2$)$_2$—.

6. A compound according to claim 1 in which Z is —(CH$_2$)$_3$—.

7. A compound according to claim 1 in which Z is —NH—.

8. A compound according to claim 1 in which Z is —N(CH$_3$)CH$_2$.

9. A compound according to claim 1 in which R1 is hydrogen or an ethyl group.

10. A compound according to claim 1 in which R3 contains a phenyl moiety which is substituted in the 4-position.

11. A compound according to claim 1 which is in the form of a fumarate salt.

12. A pharmaceutical composition which comprises a effective anti-ischaemic amount of a compound as defined in claim 1 and a pharmaceutically acceptable excipient.

13. A method of treatment is ischaemia, which comprises administering to a subject in need or liable to be in need of such treatment an effective amount of a compound as defined in claim 1.

14. The compound according to claim 1 which is (±)5-[1-Hydroxy-2-(4-phenoxy-1-piperidyl)ethyl]-3H-indol-2-one.

* * * * *